United States Patent
Abolfathi et al.

(10) Patent No.: US 9,906,878 B2
(45) Date of Patent: *Feb. 27, 2018

(54) METHODS AND APPARATUS FOR TRANSMITTING VIBRATIONS

(71) Applicant: SoundMed, LLC, Mountain View, CA (US)

(72) Inventors: Amir Abolfathi, Petaluma, CA (US); Vahid Saadat, Atherton, CA (US); Loc X. Phan, San Jose, CA (US)

(73) Assignee: SoundMed, LLC, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/438,403

(22) Filed: Feb. 21, 2017

(65) Prior Publication Data

US 2017/0171675 A1  Jun. 15, 2017

Related U.S. Application Data

(63) Continuation of application No. 14/828,372, filed on Aug. 17, 2015, now Pat. No. 9,615,182, which is a
(Continued)

(51) Int. Cl.
  *H04R 25/00* (2006.01)
  *B33Y 80/00* (2015.01)
  (Continued)

(52) U.S. Cl.
  CPC .............. *H04R 25/606* (2013.01); *A61C 5/00* (2013.01); *A61C 8/0093* (2013.01);
  (Continued)

(58) Field of Classification Search
  CPC combination set(s) only.
  See application file for complete search history.

(56) References Cited

U.S. PATENT DOCUMENTS

| 2,045,404 A | 6/1936 | Nicholides |
| 2,161,169 A | 6/1939 | Jefferis |

(Continued)

FOREIGN PATENT DOCUMENTS

| CN | 1425264 | 6/2003 |
| EP | 0715838 A2 | 6/1996 |

(Continued)

OTHER PUBLICATIONS

"Special Forces Smart Noise Cancellation Ear Buds with Built-In GPS," http://www.gizmag.com/special-forces-smart-noise-cancellation-ear-buds-with-built-in-gps/9428/, 2 pages, 2008.

(Continued)

*Primary Examiner* — Amir Etesam
(74) *Attorney, Agent, or Firm* — Levine Bagade Han LLP

(57) ABSTRACT

Methods and apparatus for transmitting vibrations via an electronic and/or transducer assembly through a tooth or teeth are disclosed herein. The assembly may be attached, adhered, or otherwise embedded into or upon a removable oral appliance to form a hearing aid assembly. Such an oral appliance may be a custom-made device. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

17 Claims, 21 Drawing Sheets

Related U.S. Application Data continuation of application No. 14/056,821, filed on Oct. 17, 2013, now Pat. No. 9,113,262, which is a continuation of application No. 13/551,158, filed on Jul. 17, 2012, now Pat. No. 8,588,447, which is a continuation of application No. 12/333,259, filed on Dec. 11, 2008, now Pat. No. 8,254,611, which is a continuation of application No. 11/754,823, filed on May 29, 2007, now Pat. No. 7,844,064.

(60) Provisional application No. 60/809,244, filed on May 30, 2006, provisional application No. 60/820,223, filed on Jul. 24, 2006.

(51) Int. Cl.
*A61C 5/00* (2017.01)
*A61C 8/00* (2006.01)
*H04R 1/46* (2006.01)
*H04R 3/04* (2006.01)
*B33Y 70/00* (2015.01)

(52) U.S. Cl.
CPC ............ *A61C 8/0098* (2013.01); *B33Y 80/00* (2014.12); *H04R 1/46* (2013.01); *H04R 3/04* (2013.01); *H04R 25/554* (2013.01); *H04R 25/602* (2013.01); *B33Y 70/00* (2014.12); *H04R 25/604* (2013.01); *H04R 2225/31* (2013.01); *H04R 2225/67* (2013.01); *H04R 2420/07* (2013.01); *H04R 2460/01* (2013.01); *H04R 2460/13* (2013.01)

(56) References Cited

U.S. PATENT DOCUMENTS

| | | |
|---|---|---|
| 2,230,397 A | 2/1941 | Abraham |
| 2,242,118 A | 5/1941 | Fischer |
| 2,318,872 A | 5/1943 | Madiera |
| 2,977,425 A | 3/1961 | Cole |
| 2,995,633 A | 8/1961 | Puharich et al. |
| 3,156,787 A | 11/1964 | Puharich et al. |
| 3,170,993 A | 2/1965 | Puharich et al. |
| 3,267,931 A | 8/1966 | Puharich et al. |
| 3,325,743 A | 6/1967 | Blum |
| 3,712,962 A | 1/1973 | Epley |
| 3,787,641 A | 1/1974 | Santori |
| 3,894,196 A | 7/1975 | Briskey |
| 3,985,977 A | 10/1976 | Beaty et al. |
| 4,025,732 A | 5/1977 | Traunmuller |
| 4,150,262 A | 4/1979 | Ono |
| 4,498,461 A | 2/1985 | Hakansson |
| 4,591,668 A | 5/1986 | Iwata |
| 4,612,915 A | 9/1986 | Hough et al. |
| 4,642,769 A | 2/1987 | Petrofsky |
| 4,738,268 A | 4/1988 | Kipnis |
| 4,791,673 A | 12/1988 | Schreiber |
| 4,817,044 A | 3/1989 | Ogren |
| 4,832,033 A | 5/1989 | Maher et al. |
| 4,904,233 A | 2/1990 | Haakansson et al. |
| 4,920,984 A | 5/1990 | Furumichi et al. |
| 4,962,559 A | 10/1990 | Schuman |
| 4,982,434 A | 1/1991 | Lenhardt et al. |
| 5,012,520 A | 4/1991 | Steeger |
| 5,033,999 A | 7/1991 | Mersky |
| 5,047,994 A | 9/1991 | Lenhardt et al. |
| 5,060,526 A | 10/1991 | Barth et al. |
| 5,082,007 A | 1/1992 | Adell |
| 5,233,987 A | 8/1993 | Fabian et al. |
| 5,323,468 A | 6/1994 | Bottesch |
| 5,325,436 A | 6/1994 | Soli et al. |
| 5,354,326 A | 10/1994 | Comben et al. |
| 5,372,142 A | 12/1994 | Madsen et al. |
| 5,402,496 A | 3/1995 | Soli et al. |
| 5,403,262 A | 4/1995 | Gooch |
| 5,447,489 A * | 9/1995 | Issalene ............... H04R 25/606 128/864 |
| 5,455,842 A | 10/1995 | Merskey et al. |
| 5,460,593 A | 10/1995 | Mersky et al. |
| 5,477,489 A | 12/1995 | Wiedmann |
| 5,546,459 A | 8/1996 | Sih et al. |
| 5,558,618 A | 9/1996 | Maniglia |
| 5,565,759 A | 10/1996 | Dunstan |
| 5,579,284 A | 11/1996 | May |
| 5,616,027 A | 4/1997 | Jacobs et al. |
| 5,624,376 A | 4/1997 | Ball et al. |
| 5,661,813 A | 8/1997 | Shimauchi et al. |
| 5,706,251 A | 1/1998 | May |
| 5,760,692 A | 6/1998 | Block |
| 5,793,875 A | 8/1998 | Lehr et al. |
| 5,800,336 A | 9/1998 | Ball et al. |
| 5,812,496 A | 9/1998 | Peck |
| 5,828,765 A | 10/1998 | Gable |
| 5,902,167 A | 5/1999 | Filo et al. |
| 5,914,701 A | 6/1999 | Gersheneld et al. |
| 5,961,443 A | 10/1999 | Rastatter et al. |
| 5,984,681 A | 11/1999 | Huang |
| 6,029,558 A | 2/2000 | Stevens et al. |
| 6,047,074 A | 4/2000 | Zoels et al. |
| 6,057,668 A | 5/2000 | Chao |
| 6,068,590 A | 5/2000 | Brisken |
| 6,072,884 A | 6/2000 | Kates |
| 6,072,885 A | 6/2000 | Stockham, Jr. et al. |
| 6,075,557 A | 6/2000 | Holliman et al. |
| 6,115,477 A | 9/2000 | Filo et al. |
| 6,118,882 A | 9/2000 | Haynes |
| 6,171,229 B1 | 1/2001 | Kroll et al. |
| 6,223,018 B1 | 4/2001 | Fukumoto et al. |
| 6,239,705 B1 | 5/2001 | Glen |
| 6,333,269 B2 | 12/2001 | Naito et al. |
| 6,371,758 B1 | 4/2002 | Kittelsen |
| 6,377,693 B1 | 4/2002 | Lippa et al. |
| 6,394,969 B1 | 5/2002 | Lenhardt |
| 6,504,942 B1 | 1/2003 | Hong et al. |
| 6,533,747 B1 | 3/2003 | Polaschegg et al. |
| 6,538,558 B2 | 3/2003 | Sakazume et al. |
| 6,585,637 B2 | 7/2003 | Brillhart et al. |
| 6,629,922 B1 | 10/2003 | Puria et al. |
| 6,631,197 B1 | 10/2003 | Taenzer |
| 6,633,747 B1 | 10/2003 | Reiss |
| 6,658,124 B1 | 12/2003 | Meadows |
| 6,682,472 B1 | 1/2004 | Davis |
| 6,694,035 B1 | 2/2004 | Teicher et al. |
| 6,754,472 B1 | 6/2004 | Williams et al. |
| 6,778,674 B1 | 8/2004 | Panasik et al. |
| 6,826,284 B1 | 11/2004 | Benesty et al. |
| 6,885,753 B2 | 4/2005 | Bank |
| 6,917,688 B2 | 7/2005 | Yu et al. |
| 6,941,952 B1 | 9/2005 | Rush, III |
| 6,954,668 B1 | 10/2005 | Cuozzo |
| 6,985,599 B2 | 1/2006 | Asnes |
| 7,003,099 B1 | 2/2006 | Zhang et al. |
| 7,010,139 B1 | 3/2006 | Smeehuyzen |
| 7,033,313 B2 | 4/2006 | Lupin et al. |
| 7,035,415 B2 | 4/2006 | Belt et al. |
| 7,074,222 B2 | 7/2006 | Westerkull |
| 7,076,077 B2 | 7/2006 | Atsumi et al. |
| 7,099,822 B2 | 8/2006 | Zangi |
| 7,162,420 B2 | 1/2007 | Zangi et al. |
| 7,171,003 B1 | 1/2007 | Venkatesh et al. |
| 7,171,008 B2 | 1/2007 | Elko |
| 7,174,022 B1 | 2/2007 | Zhang et al. |
| 7,174,026 B2 | 2/2007 | Niederdränk |
| 7,206,423 B1 | 4/2007 | Feng et al. |
| 7,246,058 B2 | 7/2007 | Burnett |
| 7,258,533 B2 | 8/2007 | Tanner et al. |
| 7,269,266 B2 | 9/2007 | Anjanappa et al. |
| 7,271,569 B2 | 9/2007 | Oglesbee |
| 7,281,924 B2 | 10/2007 | Ellison |
| 7,310,427 B2 | 12/2007 | Retchin et al. |
| 7,329,226 B1 | 2/2008 | Ni et al. |
| 7,331,349 B2 | 2/2008 | Brady et al. |
| 7,333,624 B2 | 2/2008 | Husung |
| 7,361,216 B2 | 4/2008 | Kangas et al. |

(56) References Cited

U.S. PATENT DOCUMENTS

| | | |
|---|---|---|
| 7,409,070 B2 | 8/2008 | Pitulia |
| 7,486,798 B2 | 2/2009 | Anjanappa et al. |
| 7,512,448 B2 | 3/2009 | Malick et al. |
| 7,520,851 B2 | 4/2009 | Davis et al. |
| 7,522,738 B2 | 4/2009 | Miller, III |
| 7,522,740 B2 | 4/2009 | Julstrom et al. |
| 7,664,277 B2 | 2/2010 | Abolfathi et al. |
| 7,680,284 B2 | 3/2010 | Lee et al. |
| 7,724,911 B2 | 5/2010 | Menzel et al. |
| 7,796,769 B2 | 9/2010 | Abolfathi |
| 7,801,319 B2 | 9/2010 | Abolfathi |
| 7,844,064 B2 | 11/2010 | Abolfathi et al. |
| 7,844,070 B2 | 11/2010 | Abolfathi |
| 7,876,906 B2 | 1/2011 | Abolfathi |
| 8,189,838 B1 | 5/2012 | Rich |
| 8,254,611 B2 | 8/2012 | Abolfathi et al. |
| 8,270,638 B2 | 9/2012 | Abolfathi et al. |
| 8,588,447 B2 | 11/2013 | Abolfathi et al. |
| 8,649,535 B2 | 2/2014 | Menzel et al. |
| 9,049,527 B2 | 6/2015 | Andersson et al. |
| 2001/0003788 A1 | 6/2001 | Ball et al. |
| 2001/0051776 A1 | 12/2001 | Lenhardt |
| 2002/0026091 A1 | 2/2002 | Leysieffer |
| 2002/0039427 A1 | 4/2002 | Whitwell et al. |
| 2002/0071581 A1 | 6/2002 | Leysieffer et al. |
| 2002/0077831 A1 | 6/2002 | Numa |
| 2002/0122563 A1 | 9/2002 | Schumaier |
| 2002/0173697 A1 | 11/2002 | Lenhardt |
| 2003/0048915 A1 | 3/2003 | Bank |
| 2003/0059078 A1 | 3/2003 | Downs et al. |
| 2003/0091200 A1 | 5/2003 | Pompei |
| 2003/0212319 A1 | 11/2003 | Magill |
| 2004/0057591 A1 | 3/2004 | Beck et al. |
| 2004/0063073 A1 | 4/2004 | Kajimoto et al. |
| 2004/0131200 A1 | 7/2004 | Davis |
| 2004/0141624 A1 | 7/2004 | Davis et al. |
| 2004/0202339 A1 | 10/2004 | O'Brien, Jr. et al. |
| 2004/0202344 A1 | 10/2004 | Anjanappa et al. |
| 2004/0214130 A1 | 10/2004 | Fischer et al. |
| 2004/0243481 A1 | 12/2004 | Bradbury et al. |
| 2004/0247143 A1 | 12/2004 | Lantrua et al. |
| 2005/0037312 A1 | 2/2005 | Uchida |
| 2005/0067816 A1 | 3/2005 | Buckman |
| 2005/0070782 A1 | 3/2005 | Brodkin |
| 2005/0129257 A1 | 6/2005 | Tamura |
| 2005/0189910 A1 | 9/2005 | Hui |
| 2005/0196008 A1 | 9/2005 | Anjanappa et al. |
| 2005/0241646 A1 | 11/2005 | Sotos et al. |
| 2006/0008106 A1 | 1/2006 | Harper |
| 2006/0025648 A1 | 2/2006 | Lupin et al. |
| 2006/0064037 A1 | 3/2006 | Shalon et al. |
| 2006/0167335 A1 | 7/2006 | Park et al. |
| 2006/0207611 A1 | 9/2006 | Anonsen |
| 2006/0270467 A1 | 11/2006 | Song et al. |
| 2006/0275739 A1 | 12/2006 | Ray |
| 2007/0010704 A1 | 1/2007 | Pitulia |
| 2007/0035917 A1 | 2/2007 | Hotelling et al. |
| 2007/0036370 A1 | 2/2007 | Granovetter et al. |
| 2007/0041595 A1 | 2/2007 | Carazo et al. |
| 2007/0105072 A1 | 5/2007 | Koljonen |
| 2007/0142072 A1 | 6/2007 | Lassally |
| 2007/0223735 A1 | 9/2007 | LoPresti et al. |
| 2007/0230713 A1 | 10/2007 | Davis |
| 2007/0242835 A1 | 10/2007 | Davis |
| 2007/0265533 A1 | 11/2007 | Tran |
| 2007/0276270 A1 | 11/2007 | Tran |
| 2007/0280491 A1 | 12/2007 | Abolfathi |
| 2007/0280492 A1 | 12/2007 | Abolfathi |
| 2007/0280493 A1 | 12/2007 | Abolfathi |
| 2007/0280495 A1 | 12/2007 | Abolfathi |
| 2007/0286440 A1 | 12/2007 | Abolfathi et al. |
| 2007/0291972 A1 | 12/2007 | Abolfathi et al. |
| 2008/0019542 A1 | 1/2008 | Menzel et al. |
| 2008/0019557 A1 | 1/2008 | Bevirt et al. |
| 2008/0021327 A1 | 1/2008 | El-Bialy et al. |
| 2008/0064993 A1 | 3/2008 | Abolfathi et al. |
| 2008/0070181 A1 | 3/2008 | Abolfathi et al. |
| 2008/0109972 A1 | 5/2008 | Mah et al. |
| 2008/0205678 A1 | 8/2008 | Boglavskij et al. |
| 2008/0304677 A1 | 12/2008 | Abolfathi et al. |
| 2009/0028352 A1 | 1/2009 | Petroff |
| 2009/0052698 A1 | 2/2009 | Rader et al. |
| 2009/0088598 A1 | 4/2009 | Abolfathi |
| 2009/0097684 A1 | 4/2009 | Abolfathi et al. |
| 2009/0097685 A1 | 4/2009 | Menzel et al. |
| 2009/0099408 A1 | 4/2009 | Abolfathi et al. |
| 2009/0105523 A1 | 4/2009 | Kassayan et al. |
| 2009/0147976 A1 | 6/2009 | Abolfathi |
| 2009/0149722 A1 | 6/2009 | Abolfathi et al. |
| 2009/0180652 A1 | 7/2009 | Davis et al. |
| 2009/0220115 A1 | 9/2009 | Lantrua |
| 2009/0226020 A1 | 9/2009 | Abolfathi |
| 2010/0189288 A1 | 7/2010 | Menzel et al. |
| 2010/0220883 A1 | 9/2010 | Menzel et al. |
| 2010/0312568 A1 | 12/2010 | Abolfathi |
| 2010/0322449 A1 | 12/2010 | Abolfathi |
| 2011/0002492 A1 | 1/2011 | Abolfathi et al. |
| 2011/0026740 A1 | 2/2011 | Abolfathi |
| 2011/0116659 A1 | 5/2011 | Abolfathi |
| 2012/0321113 A1 | 12/2012 | Abolfathi |
| 2013/0003996 A1 | 1/2013 | Menzel et al. |
| 2013/0010987 A1 | 1/2013 | Abolfathi et al. |

FOREIGN PATENT DOCUMENTS

| | | |
|---|---|---|
| EP | 0824889 A1 | 2/1998 |
| EP | 1783919 A1 | 5/2007 |
| GB | 1066299 A | 4/1967 |
| JP | 56-026490 | 3/1981 |
| JP | 2007028248 A2 | 2/2007 |
| JP | 2007028610 A2 | 2/2007 |
| JP | 2007044284 A2 | 2/2007 |
| JP | 2007049599 A2 | 2/2007 |
| JP | 2007049658 A2 | 2/2007 |
| WO | WO 1983/002047 | 6/1983 |
| WO | WO 1991/002678 | 3/1991 |
| WO | WO 1995/006398 | 3/1995 |
| WO | WO 1995/019678 | 7/1995 |
| WO | WO 1996/021335 | 7/1996 |
| WO | WO 2002/009622 | 2/2002 |
| WO | WO 2003/001845 | 1/2003 |
| WO | WO 2004/045242 | 5/2004 |
| WO | WO 2004/093493 | 10/2004 |
| WO | WO 2004/105650 | 12/2004 |
| WO | WO 2005/000391 | 1/2005 |
| WO | WO 2005/037153 | 4/2005 |
| WO | WO 2005/053533 | 6/2005 |
| WO | WO 2006/044161 | 4/2006 |
| WO | WO 2006/088410 | 8/2006 |
| WO | WO 2006/130909 | 12/2006 |
| WO | WO 2007/043055 | 4/2007 |
| WO | WO 2007/052251 | 5/2007 |
| WO | WO 2007/059185 | 5/2007 |
| WO | WO 2007/140367 | 12/2007 |
| WO | WO 2007/140368 | 12/2007 |
| WO | WO 2007/140373 | 12/2007 |
| WO | WO 2007/143453 | 12/2007 |
| WO | WO 2008/024794 | 2/2008 |
| WO | WO 2008/030725 | 3/2008 |
| WO | WO 2009/014812 | 1/2009 |
| WO | WO 2009/025917 | 2/2009 |
| WO | WO 2009/066296 | 5/2009 |
| WO | WO 2009/102889 | 8/2009 |
| WO | WO 2009/111404 | 9/2009 |
| WO | WO 2009/111566 | 9/2009 |

OTHER PUBLICATIONS

Altmann, et al. Foresighting the new technology waves—Exper Group. In: State of the Art Reviews and Related Papers—Center on Nanotechnology and Society. 2004 Conference. Published Jun. 14, 2004, p. 1-291. Available at http://www.nano-and-society.org/

(56) References Cited

OTHER PUBLICATIONS

NELSI/documents/ECreviewsandpapers061404.pdf. Accessed Jan. 11, 2009.
Berard, G., "Hearing Equals Behavior" [summary], 1993, http://www.bixby.org/faq/tinnitus/treatment.html.
Bozkaya, D. et al., "Mechanics of the Tapered Interference Fit in Dental Implants," published Oct. 2002 [online], retrieved Oct. 14, 2010. http://www1.coe.neu.edu/~smuftu/Papers/paper-interference-fit-elsevier-2.pdf.
Broyhill, D., "Battlefield Medical Information System—Telemedicine," A research paper presented to the U.S. Army Command and General Staff College in partial Fulfillment of the requirement for A462 Combat Health Support Seminar, 12 pages, 2003.
Dental Cements—Premarket Notification, U.S. Department of Health and Human Services Food and Drug Administration Center for Devices and Radiological Health, pp. 1-10, Aug. 18, 1998.
Henry, et al. "Comparison of Custom Sounds for Achieving Tinnitus Relief," *J Am Acad Audiol*, 15:585-598, 2004.
Jastreboff, Pawel, J., "Phantom auditory perception (tinnitus): mechanisms of generation and perception," *Neuroscience Research*, 221-254, 1990, Elsevier Scientific Publishers Ireland, Ltd.
Robb, "Tinnitus Device Directory Part I," *Tinnitus Today*, p. 22, Jun. 2003.
Song, S. et al., "A 0.2-mW 2-Mb/s Digital Transceiver Based on Wideband Signaling for Human Body Communications," *IEEE J Solid-State Cir*, 42(9), 2021-2033, Sep. 2007.
Stuart, A., et al., "Investigations of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].
Wen, Y. et al, "Online Prediction of Battery Lifetime for Embedded and Mobile Devices," Special Issue on Embedded Systems: Springer-Verlag Heidelberg Lecture Notes in Computer Science, V3164/2004, 15 pages, Dec. 2004.

\* cited by examiner

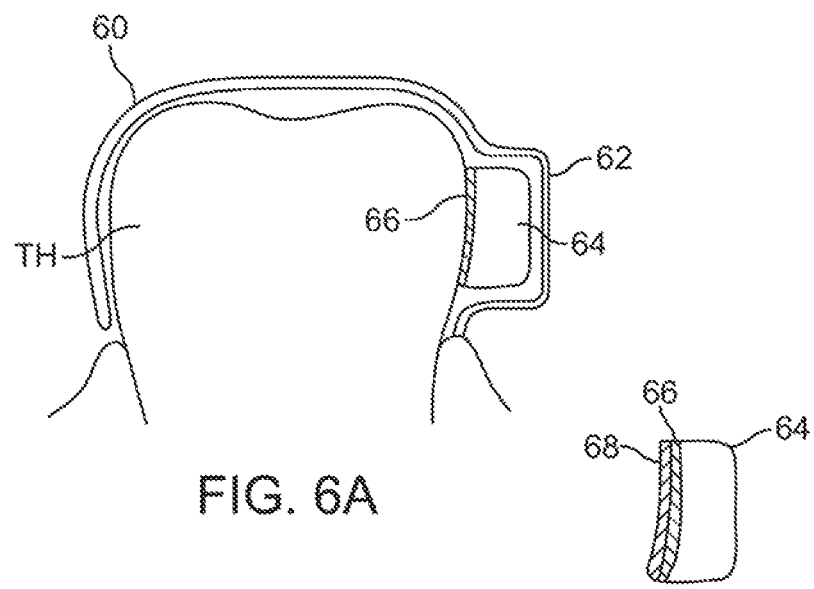
FIG. 6A
FIG. 6B
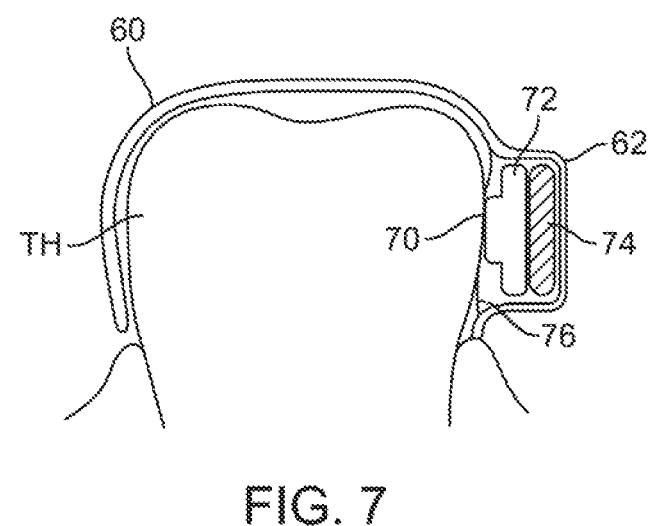
FIG. 7

METHODS AND APPARATUS FOR TRANSMITTING VIBRATIONS

CROSS-REFERENCE TO RELATED APPLICATIONS

This application is a continuation of U.S. patent application Ser. No. 14/828,372 filed Aug. 17, 2015, which is a continuation of U.S. patent application Ser. No. 14/056,821 filed Oct. 17, 2013 (now U.S. Pat. No. 9,113,262 issued Aug. 18, 2015), which is a continuation of U.S. patent application Ser. No. 13/551,158 filed Jul. 17, 2012 (now U.S. Pat. No. 8,588,447 issued Nov. 19, 2013), which is a continuation of U.S. patent application Ser. No. 12/333,259 filed Dec. 11, 2008 (now U.S. Pat. No. 8,254,611 issued Aug. 28, 2012), which is a continuation of U.S. patent application Ser. No. 11/754,823 filed May 29, 2007 (now U.S. Pat. No. 7,844,064 issued Nov. 30, 2010), which claims the benefit of priority to U.S. Prov. Pat Apps. 60/809,244 filed May 30, 2006 and 60/820,223 filed Jul. 24, 2006, each of which is incorporated herein by reference in its entirety.

FIELD OF THE INVENTION

The present invention relates to methods and apparatus for transmitting vibrations through teeth or bone structures in and/or around a mouth. More particularly, the present invention relates to methods and apparatus for sound conduction through teeth or bone structures in and/or around the mouth by transmitting vibrations correlating to auditory signals received by a user.

BACKGROUND OF THE INVENTION

Hearing loss affects over 31 million people in the United States (about 13% of the population). As a chronic condition, the incidence of hearing impairment rivals that of heart disease and, like heart disease, the incidence of hearing impairment increases sharply with age.

While the vast majority of those with hearing loss can be helped by a well-fitted, high quality bearing device, only 22% of the total hearing impaired population own hearing devices. Current products and distribution methods are not able to satisfy or reach over 20 million persons with hearing impairment in the U.S. alone.

Hearing loss adversely affects a person's quality of life and psychological well-being. Individuals with hearing impairment often withdraw from social interactions to avoid frustrations resulting from inability to understand conversations. Recent studies have shown that hearing impairment causes increased stress levels, reduced self-confidence, reduced sociability and reduced effectiveness in the workplace.

The human ear generally comprises three regions: the outer ear, the middle ear, and the inner ear. The outer ear generally comprises the external auricle and the ear canal, which is a tubular pathway through which sound reaches the middle ear. The outer ear is separated from the middle ear by the tympanic membrane (eardrum). The middle ear generally comprises three small bones, known as the ossicles, which form a mechanical conductor from the tympanic membrane to the inner ear. Finally, the inner ear includes the cochlea, which is a fluid-filled structure that contains a large number of delicate sensory hair cells that are connected to the auditory nerve.

Hearing loss can also be classified in terms of being conductive, sensorineural, or a combination of both. Conductive hearing impairment typically results from diseases or disorders that limit the transmission of sound through the middle ear. Most conductive impairments can be treated medically or surgically. Purely conductive hearing loss represents a relatively small portion of the total hearing impaired population (estimated at less than 5% of the total hearing impaired population).

Sensorineural hearing losses occur mostly in the inner ear and account for the vast majority of hearing impairment (estimated at 90-95% of the total hearing impaired population). Sensorineural hearing impairment (sometimes called "nerve loss") is largely caused by damage to the sensory hair cells inside the cochlea. Sensorineural hearing impairment occurs naturally as a result of aging or prolonged exposure to loud music and noise. This type of hearing loss cannot be reversed nor can it be medically or surgically treated; however, the use of properly fined hearing devices can improve the individual's quality of life.

Conventional hearing devices are the most common devices used to treat mild to severe sensorineural hearing impairment. These are acoustic devices that amplify sound to the tympanic membrane. These devices are individually customizable to the patient's physical and acoustical characteristics over four to six separate visits to an audiologist or hearing instrument specialist. Such devices generally comprise a microphone, amplifier, battery, and speaker. Recently, hearing device manufacturers have increased the sophistication of sound processing, often using digital technology, to provide features such as programmability and multi-band compression. Although these devices have been miniaturized and are less obtrusive, they are still visible and have major acoustic limitation.

Industry research has shown that the primary obstacles for not purchasing a hearing device generally include: a) the stigma associated with wearing a hearing device; b) dissenting attitudes on the part of the medical profession, particularly ENT physicians; c) product value issues related to perceived performance problems; d) general lack of information and education at the consumer and physician level; and e) negative word-of-mouth from dissatisfied users.

Other devices such as cochlear implants have been developed for people who have severe to profound hearing loss and are essentially deaf (approximately 2% of the total hearing impaired population). The electrode of a cochlear implant is inserted into the inner ear in an invasive and non-reversible surgery. The electrode electrically stimulates the auditory nerve through an electrode array that provides audible cues to the user, which are not usually interpreted by the brain as normal sound. Users generally require intensive and extended counseling and training following surgery to achieve the expected benefit.

Other devices such as electronic middle ear implants generally are surgically placed within the middle ear of the hearing impaired. They are surgically implanted devices with an externally worn component.

The manufacture, fitting and dispensing of hearing devices remain an arcane and inefficient process. Most hearing devices are custom manufactured, fabricated by the manufacturer to fit the ear of each prospective purchaser. An impression of the ear canal is taken by the dispenser (either an audiologist or licensed hearing instrument specialist) and mailed to the manufacturer for interpretation and fabrication of the custom molded rigid plastic casing. Hand-wired electronics and transducers (microphone and speaker) are then placed inside the casing, and the final product is shipped back to the dispensing professional after some period of time, typically one to two weeks.

The time cycle for dispensing a hearing device, from the first diagnostic session to the final fine-tuning session, typically spans a period over several weeks, such as six to eight weeks, and involves multiple with the dispenser.

Accordingly, there exists a need for methods and devices which are efficacious and safe in facilitating the treatment of hearing loss in patients.

SUMMARY OF THE INVENTION

An electronic and transducer device may be attached, adhered, or otherwise embedded into or upon a removable dental or oral appliance to form a hearing aid assembly. Such a removable oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

The assembly for transmitting vibrations via at least one tooth may generally comprise a housing having a shape which is conformable to at least a portion of the at least one tooth, and an actuatable transducer disposed within or upon the housing and in vibratory communication with a surface of the at least one tooth. Moreover, the transducer itself may be a separate assembly from the electronics and may be positioned along another surface of the tooth, such as the occlusal surface, or even attached to an implanted post or screw embedded into the underlying bone. Additionally, the transducer may also be placed directly onto the gingival tissue surface adjacent to the tooth for vibratory transmission through the tissue and into the underlying bone.

One example of a method for transmitting these vibrations via at least one tooth may generally comprising positioning a housing of the removable oral appliance onto at least one tooth, whereby the housing has a shape which is conformable to at least a portion of the tooth, and maintaining contact between a surface of the tooth with an actuatable transducer such that the surface and transducer remain in vibratory communication.

BRIEF DESCRIPTION OF THE DRAWINGS

FIG. 6A shows a partial cross-sectional view of an oral appliance placed upon a tooth with an electronics/transducer assembly adhered to the tooth surface via an adhesive.

FIG. 6B shows a partial cross-sectional view of a removable backing adhered onto an adhesive surface.

FIG. 7 shows a partial cross-sectional view of another variation of an oral appliance placed upon a tooth with an electronics/transducer assembly pressed against the tooth surface via an osmotic pouch.

FIG. 14 shows yet another variation of an oral appliance having a cam mechanism for urging the electronics and/or transducer assembly against the tooth surface.

DETAILED DESCRIPTION OF THE INVENTION

An electronic and transducer device may be attached, adhered, or otherwise embedded into or upon a removable oral appliance or other oral device to form a hearing aid assembly. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1:
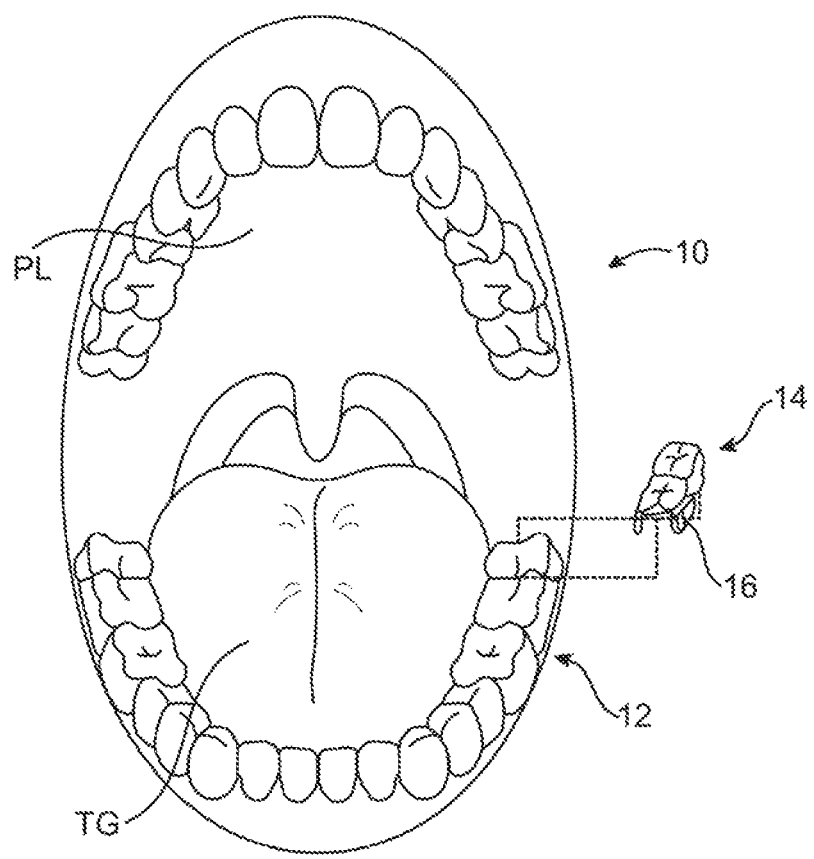
FIG. 1 illustrates the dentition of a patient's teeth and one variation of a hearing aid device which is removably placed upon or against the patient's tooth or teeth as a removable oral appliance.

As shown in FIG. 1, a patient's mouth and dentition 10 is illustrated showing one possible location for removably attaching hearing aid assembly 14 upon or against at least one tooth, such as a molar 12. The patient's tongue TG and palate PL are also illustrated for reference. An electronics and/or transducer assembly 16 may be attached, adhered, or otherwise embedded into or upon the assembly 14, as described below in further detail.

Figure 2A:
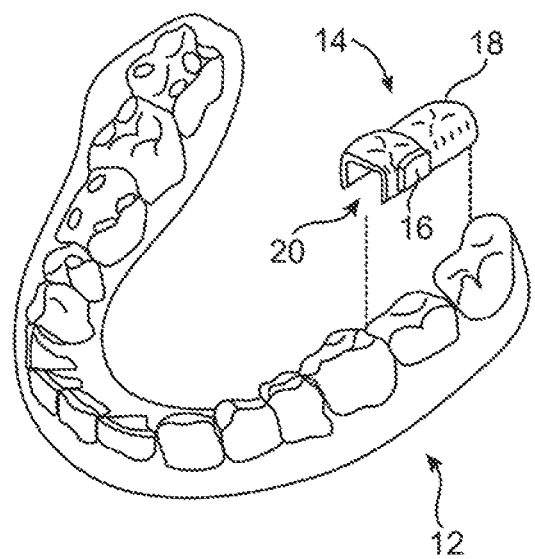
FIG. 2A illustrates a perspective view of the lower teeth showing one exemplary location for placement of the removable oral appliance hearing aid device.

FIG. 2A shows a perspective view of the patient's lower dentition illustrating the hearing aid assembly 14 comprising a removable oral appliance 18 and the electronics and/or transducer assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or transducer assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein.

Figure 2B:
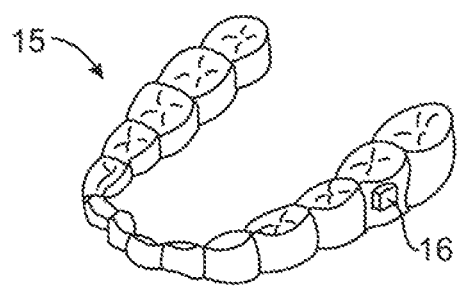
FIG. 2B illustrates another variation of the removable oral appliance in the form of an appliance which is placed over an entire row of teeth in the manner of a mouthguard.

FIG. 2B shows another variation of a removable oral appliance in the form of an appliance 15 which is placed over an entire row of teeth in the manner of a mouthguard. In this variation, appliance 15 may be configured to cover an entire bottom row of teeth or alternatively an entire upper row of teeth. In additional variations, rather than covering the entire rows of teeth, a majority of the row of teeth may be instead be covered by appliance 15. Assembly 16 may be positioned along one or more portions of the oral appliance 15.

Figure 2C:
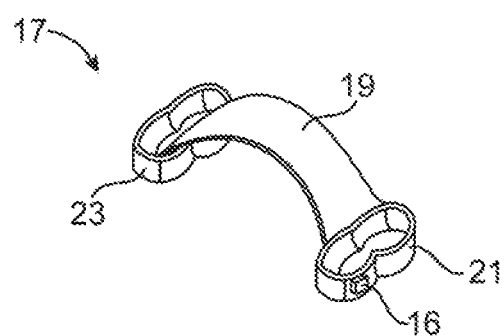
FIG. 2C illustrates another variation of the removable oral appliance which is supported by an arch.

FIG. 2C shows yet another variation of an oral appliance 17 having an arched configuration. In this appliance, one or more tooth retaining portions 21, 23, which in this variation may be placed along the upper row of teeth, may be supported by an arch 19 which may lie adjacent or along the palate of the user. As shown, electronics and/or transducer assembly 16 may be positioned along one or more portions of the tooth retaining portions 21, 23. Moreover, although the variation shown illustrates an arch 19 which may cover only a portion of the palate of the user, other variations may be configured to have an arch which covers the entire palate of the user.

Figure 2D:
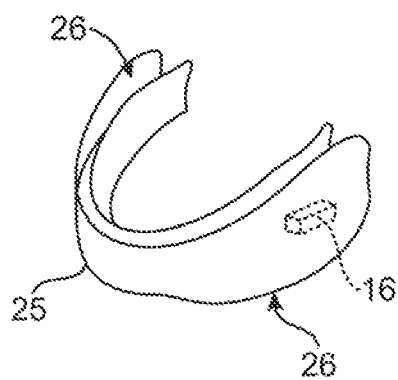
FIG. 2D illustrates another variation of an oral appliance configured as a mouthguard.

FIG. 2D illustrates yet another variation of an oral appliance in the form of a mouthguard or retainer 25 which may be inserted and removed easily from the user's mouth. Such a mouthguard or retainer 25 may be used in sports where conventional mouthguards are worn; however, mouthguard or retainer 25 having assembly 16 integrated therein may be utilized by persons, hearing impaired or otherwise, who may simply hold the mouthguard or retainer 25 via grooves or channels 26 between their teeth for receiving instructions remotely and communicating over a distance.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g., stereolithography apparatus (SLA), selective laser sintering (SLS), and/or other similar processes utilizing three-dimensional geometry of the patient's dentition, which may be obtained via any number of techniques. Such techniques may include use of scanned dentition using intra-oral scanners such as laser, white light, ultrasound, mechanical three-dimensional touch scanners, magnetic resonance imaging (MRI), computed tomography (CT), other optical methods, etc.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the transducer assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth as the appliance 18 may have a resulting size slightly smaller than the scanned tooth or teeth upon which the appliance 18 was formed. The fitting may result in a secure interference fit between the appliance 18 and underlying dentition.

Figure 3:
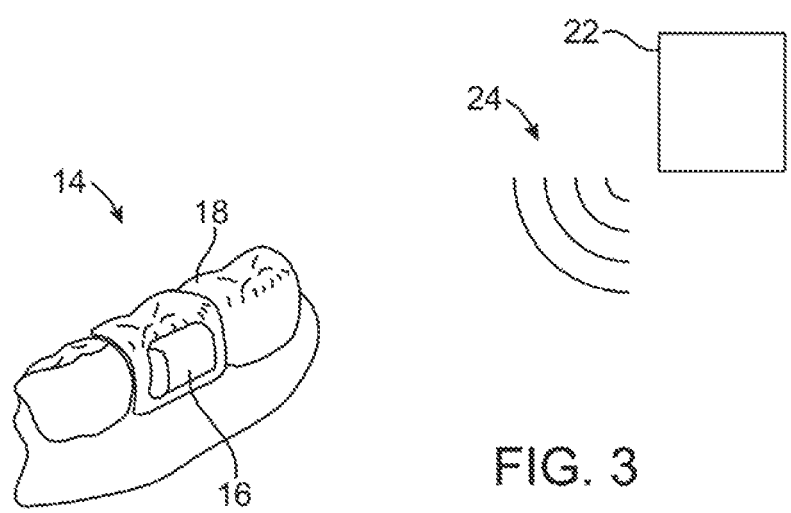
FIG. 3 illustrates a detail perspective view of the oral appliance positioned upon the patient's teeth utilizable in combination with a transmitting assembly external to the mouth and wearable by the patient in another variation of the device.

In one variation, with assembly 14 positioned upon the teeth, as shown in FIG. 3, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.)

Figure 4:
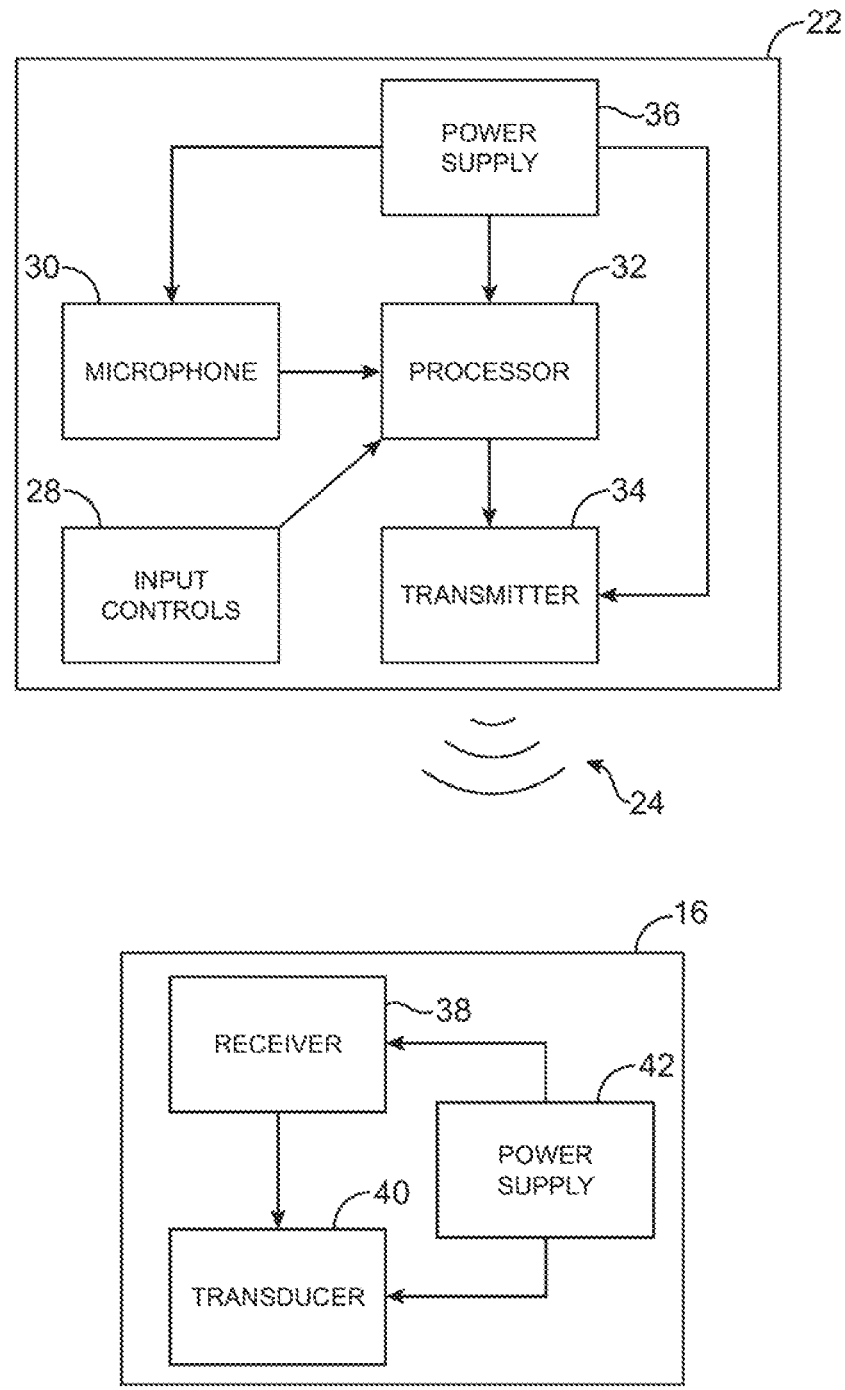
FIG. 4 shows an illustrative configuration of the individual components in a variation of the oral appliance device having an external transmitting assembly with a receiving and transducer assembly within the mouth.

FIG. 4 illustrates a schematic representation of one variation of hearing aid assembly 14 utilizing an extra-buccal transmitter assembly 22, which may generally comprise microphone 30 for receiving sounds and which is electrically connected to processor 32 for processing the auditory signals. Processor 32 may be connected electrically to transmitter 34 for transmitting the processed signals to the electronics and/or transducer assembly 16 disposed upon or adjacent to the user's teeth. The microphone 30 and processor 32 may be configured to detect and process auditory signals in any practicable range, but may be configured in one variation to detect auditory signals ranging from, e.g., 250 Hertz to 20,000 Hertz.

With respect to microphone 30, a variety of various microphone systems may be utilized. For instance, microphone 30 may be a digital, analog, and/or directional type microphone. Such various types of microphones may be interchangeably configured to be utilized with the assembly, if so desired.

Power supply 36 may be connected to each of the components in transmitter assembly 22 to provide power thereto. The transmitter signals 24 may be in any wireless form utilizing, e.g., radio frequency, ultrasound, microwave, Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted 24 by transmitter 34 may be received by electronics and/or transducer assembly 16 via receiver 38, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 4000 Hz.

Power supply 42 may also be included with assembly 16 to provide power to the receiver, transducer, and/or processor, if also included Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism, such as an internal pendulum or slidable electrical inductance charger as known in the art, which is actuated via, e.g., motions of the jaw and/or movement for translating the mechanical motion into stored electrical energy for charging power supply 42.

Figure 5:
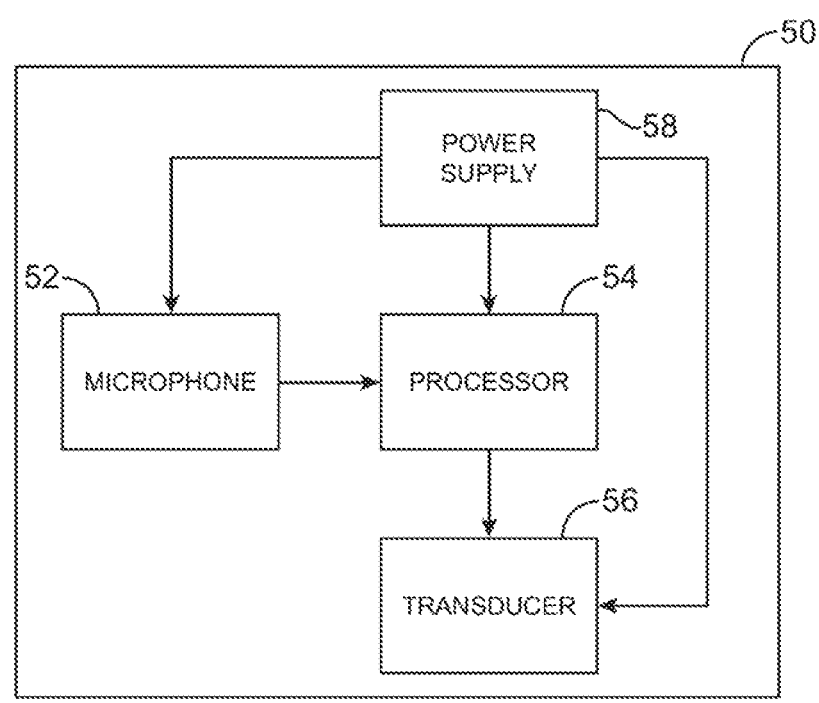
FIG. 5 shows an illustrative configuration of another variation of the device in which the entire assembly is contained by the oral appliance within the user's mouth.

In another variation of assembly 16, rather than utilizing an extra-buccal transmitter, hearing aid assembly 50 may be configured as an independent assembly contained entirely within the user's mouth, as shown in FIG. 5. Accordingly, assembly 50 may include an internal microphone 52 in communication with an on-board processor 54. Internal microphone 52 may comprise any number of different types of microphones, as described above. Processor 54 may be used to process any received auditory signals for filtering and/or amplifying the signals and transmitting them to transducer 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secure mechanical contact between the transducer and the tooth is ideally maintained to ensure efficient vibratory communication. Accordingly, any number of mechanisms may be utilized to maintain this vibratory communication.

In one variation as shown in FIG. 6A, a partial cross-sectional view of a removable oral appliance 60 is shown placed over or upon a tooth TH. Electronics and/or transducer housing 62 may be seen defined along oral appliance 60 such that housing 62 is aligned or positioned adjacent to a side surface, buccal and/or lingual surface, of the tooth TH. Housing 62 may provide protection to the electronics and/or transducer assembly from the environment of the mouth.

An electronics and/or transducer assembly 64 may be simply placed, embedded, or encapsulated within housing 62 for contacting the tooth surface. In this variation, assembly 64 may be adhered against the tooth surface via an adhesive surface or film 66 such that contact is maintained between the two. As shown in FIG. 6B, a removable backing 68 may be adhered onto adhesive surface 66 and removed prior to placement upon the tooth surface. In this manner, assembly 64 may be replaced upon the tooth as necessary with additional electronics and/or transducer assemblies.

Aside from an adhesive film 66, another alternative may utilize an expandable or swellable member to ensure a secure mechanical contact of the transducer against the tooth. As shown in FIG. 7, an osmotic patch or expandable hydrogel 74 may be placed between housing 62 and electronics and/or transducer assembly 72. After placement of oral appliance 60, hydrogel 74 may absorb some fluids, either from any surrounding fluid or from a fluid introduced into hydrogel 74, such that hydrogel 74 expands in size to force assembly 72 into contact against the tooth surface. Assembly 72 may be configured to define a contact surface 70 having a relatively smaller contact area to facilitate uniform contact of the surface 70 against the tooth. Such a contact surface 70 may be included in any of the variations described herein. Additionally, a thin encapsulating layer or surface 76 may be placed over housing 62 between contact surface 70 and the underlying tooth to prevent any debris or additional fluids from entering housing 62.

Figure 8:
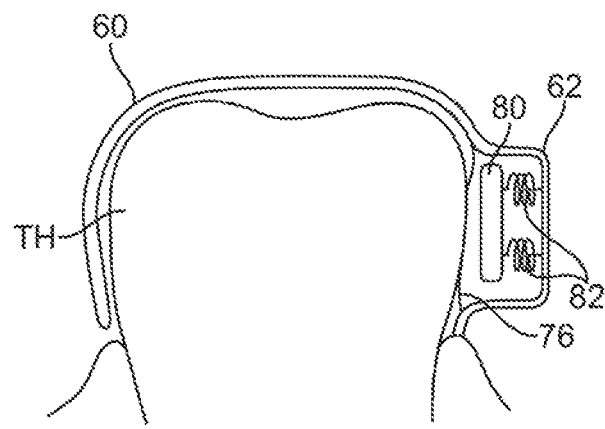
FIG. 8 shows a partial cross-sectional view of another variation of an oral appliance placed upon a tooth with an electronics/transducer assembly pressed against the tooth surface via one or more biasing elements.

Another variation is shown in FIG. 8, which shows electronics and/or transducer assembly 80 contained within housing, 62. In this variation, one or more biasing elements 82, e.g., springs, pre-formed shape memory elements, etc., may be placed between assembly 80 and housing 62 to provide a pressing force on assembly 80 to urge the device against the underlying tooth surface, thereby ensuring mechanical contact.

Figure 9:
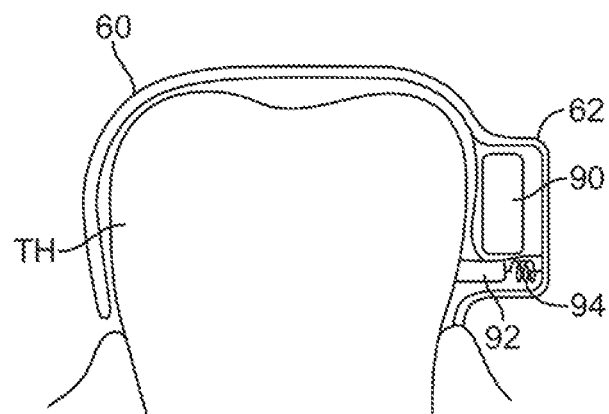
FIG. 9 illustrates another variation of an oral appliance having an electronics assembly and a transducer assembly separated from one another within the electronics and transducer housing; of the oral appliance.

In yet another variation, the electronics may be contained as a separate assembly 90 which is encapsulated within housing 62 and the transducer 92 may be maintained separately from assembly 90 but also within housing 62. As shown in FIG. 9, transducer 92 may be urged against the tooth surface via a spring or other biasing element 94 and actuated via any of the mechanisms described above.

Figure 10:
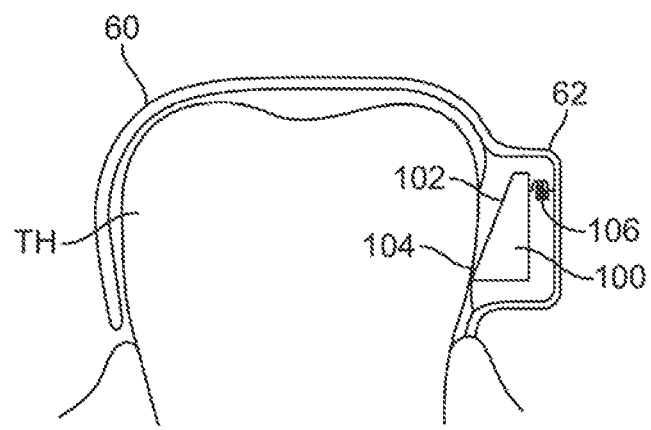
FIGS. 10 and 14 illustrate additional variations of oral appliances in which the electronics and transducer assembly are maintainable against the tooth surface via a ramped surface and a biasing element.

In other variations as shown in FIG. 10, electronics and/or transducer assembly 100 may be configured to have a ramped surface 102 in apposition to the tooth surface. The surface 102 may be angled away from the occlusal surface of the tooth. The assembly 100 may be urged via a biasing element or spring 106 which forces the ramped surface 102 to pivot about a location 104 into contact against the tooth to ensure contact for the transducer against the tooth surface.

Figure 11:
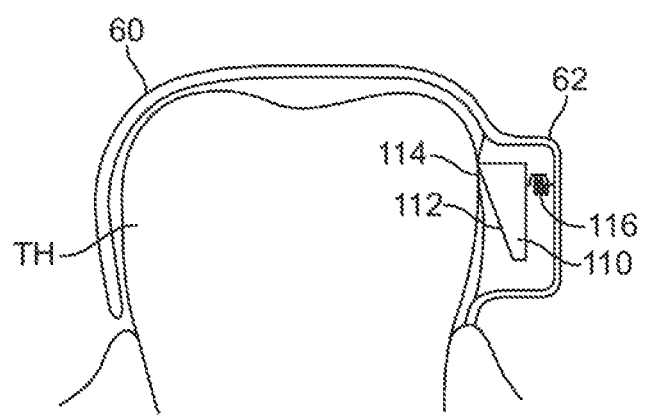

FIG. 11 illustrates another similar variation in electronics and/or transducer assembly 110 also having a ramped surface 112 in apposition to the tooth surface. In this variation, the ramped surface 112 may be angled towards the occlusal surface of the tooth. Likewise, assembly 110 may be urged via a biasing element or spring 116 which urges the assembly 110 to pivot about its lower end such that the assembly 110 contacts the tooth surface at a region 114.

Figure 12:
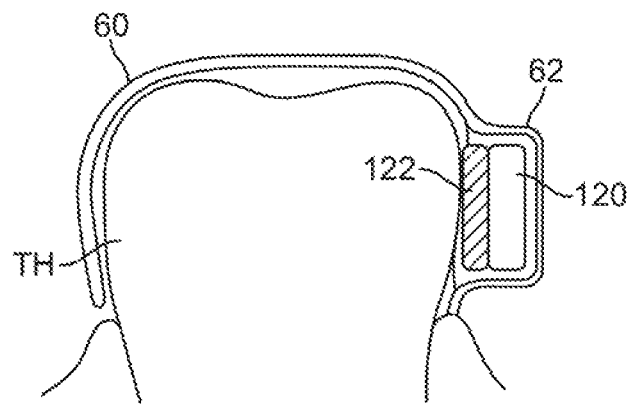
FIG. 12 shows yet another variation of an oral appliance having an interfacing member positioned between the electronics and/or transducer assembly and the tooth surface.

In yet another variation shown in FIG. 12, electronics and/or transducer assembly 120 may be positioned within housing 62 with an interface layer 122 positioned between the assembly 120 and the tooth surface. Interface layer 122 may be configured to conform against the tooth surface and against assembly 120 such that vibrations may be transmitted through layer 122 and to the tooth in a uniform manner. Accordingly, interface layer 122 may be made from a material which attenuates vibrations minimally. Interface layer 122 may be made in a variety of forms, such as a simple insert, an O-ring configuration, etc. or even in a gel or paste form, such as denture or oral paste, etc. Additionally, layer 122 may be fabricated from various materials, e.g., hard plastics or polymeric materials, metals, etc.

Figure 13:
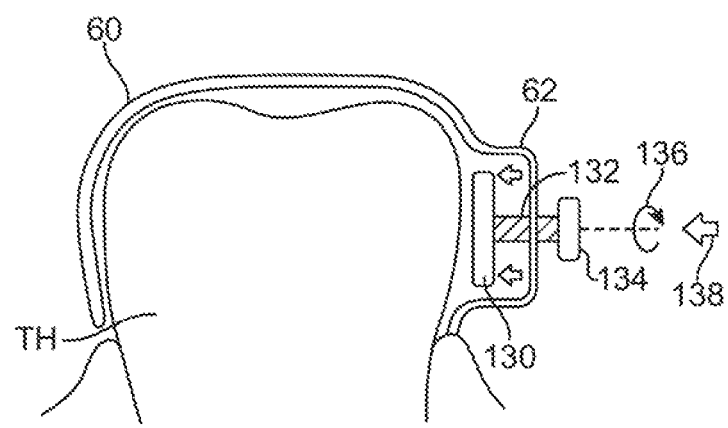
FIG. 13 shows yet another variation of an oral appliance having an actuatable mechanism for urging the electronics and/or transducer assembly against the tooth surface.

FIG. 13 illustrates yet another variation in which electronics and or transducer assembly 130 may be urged against the tooth surface via a mechanical mechanism. As shown, assembly 130 may be attached to a structural member 132, e.g., a threaded member or a simple shall, which is connected through housing 62 to an engagement member 134 located outside housing 62 The user may rotate engagement member 134 (as indicated by rotational arrow 136) or simply push upon member 134 (as indicated by linear arrow 138) to urge assembly 130 into contact against the tooth. Moreover, actuation of engagement member 134 may be accomplished manually within the mouth or through the user's cheek or even through manipulation via the user's tongue against engagement member 134.

Figure 14:
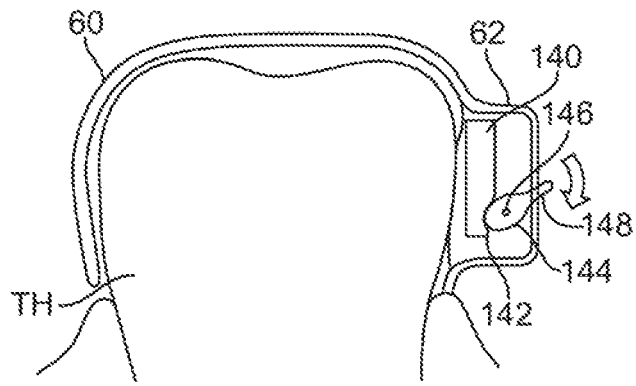

Another variation for a mechanical mechanism is illustrated in FIG. 14. In this variation, electronics and/or transducer assembly 140 may define a portion as an engaging surface 142 for contacting against a cam or lever mechanism 144. Cam or lever mechanism 144 may be configured to pivot 146 such that actuation of a lever 148 extending through housing 62 may urge cam or lever mechanism 144 to push against engaging surface 142 such that assembly 140 is pressed against the underlying tooth surface.

Figure 15:
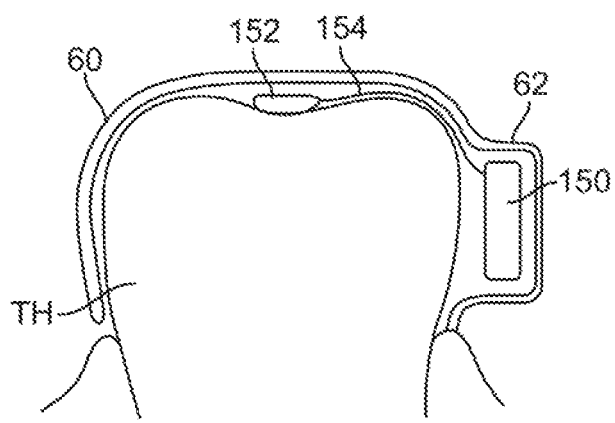
FIG. 15 shows yet another variation of an oral appliance having a separate transducer mechanism positionable upon the occlusal surface of the tooth for transmitting vibrations.

In yet another variation, the electronics 50 and the transducer 152 may be separated from one another such that electronics 150 remain disposed within housing 62 but transducer 152, connected via wire 154, is located beneath dental oral appliance 60 along an occlusal surface of the tooth, as shown in FIG. 15. In such a configuration, vibrations are transmitted via the transducer 152 through the occlusal surface of the tooth. Additionally, the user may bite down upon the oral appliance 60 and transducer 152 to mechanically compress the transducer 152 against the occlusal surface to further enhance the mechanical contact between the transducer 152 and underlying tooth to further facilitate transmission therethrough.

Figure 16:
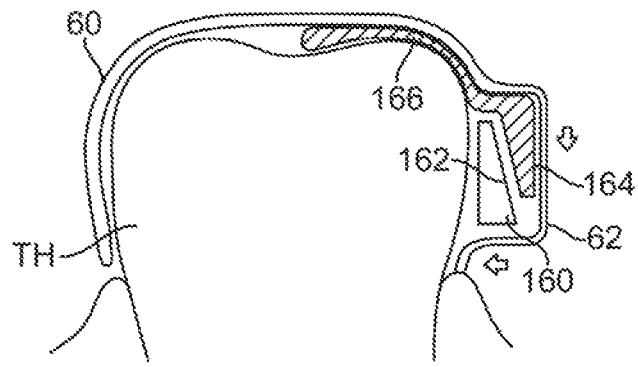
FIG. 16 illustrates another variation of an oral appliance having a mechanism for urging the electronics and/or transducer assembly against the tooth surface utilizing a bite-actuated mechanism.

In the variation of FIG. 16, another example for a bite-enhanced coupling mechanism is illustrated where electronics and/or transducer assembly 160 defines an angled interface surface 162 in apposition to a correspondingly angled engaging member 164. A proximal end of engaging member 164 may extend through housing 62 and terminate in a pusher member 166 positioned over an occlusal surface of the tooth TH. Once oral appliance 60 is initially placed over tooth TH, the user may bite down or otherwise press down upon the top portion of oral appliance 60, thereby pressing down upon pusher member 166 which in turn pushes down upon engaging member 164, as indicated by the arrow. As engaging member 164 is urged downwardly towards the gums, its angled surface may push upon the corresponding and oppositely angled surface 162 to urge assembly 160 against the tooth surface and into a secure mechanical contact.

Figure 17:
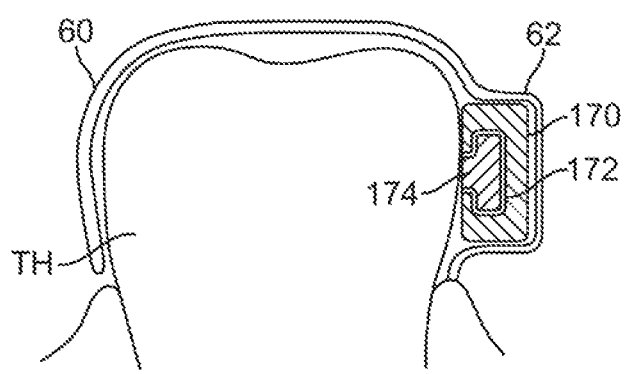
FIG. 17 shows yet another variation of an oral appliance having a composite dental anchor for coupling the transducer to the tooth.

In yet another variation, an electronics and/or transducer assembly 170 may define a channel or groove 172 along a surface for engaging a corresponding dental anchor 174, as shown in FIG. 17. Dental anchor 174 may comprise a light-curable acrylate-based composite material adhered directly to the tooth surface. Moreover dental anchor 174 may be configured in a shape which corresponds to a shape of channel or groove 172 such that the two may be interlined in a mating engagement. In this manner, the transducer in assembly 170 may vibrate directly against dental anchor 174 which may then transmit these signals directly into the tooth TH.

Figure 18A:
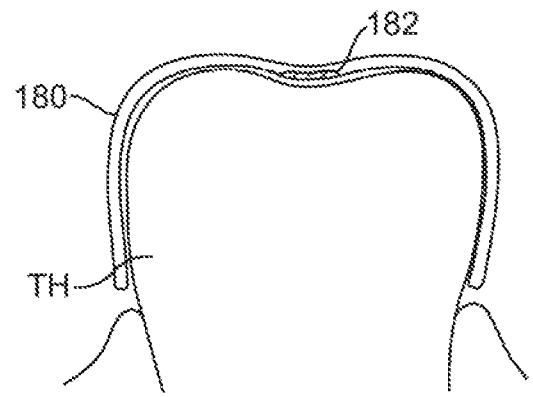
FIGS. 18A and 18B show side and top views, respectively, of an oral appliance variation having one or more transducers which may be positioned over the occlusal surface of the tooth.
Figure 18B:
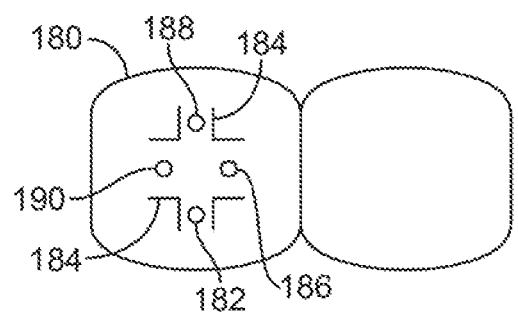

FIGS. 18A and 18B show partial cross-sectional side and top views, respectively, of another variation in which oral appliance 180 may define a number of channels or grooves 184 along a top portion of oral appliance 180. Within these channels or grooves 184, one or more transducers 182, 186, 188, 190 may be disposed such that they are in contact with the occlusal surface of the tooth and each of these transducers may be tuned to transmit frequencies uniformly. Alternatively, each of these transducers may be tuned to transmit only at specified frequency ranges. Accordingly, each transducer can be programmed or preset for a different frequency response such that each transducer may be optimized for a different frequency response and/or transmission to deliver a relatively high-fidelity sound to the user.

Figure 19A:
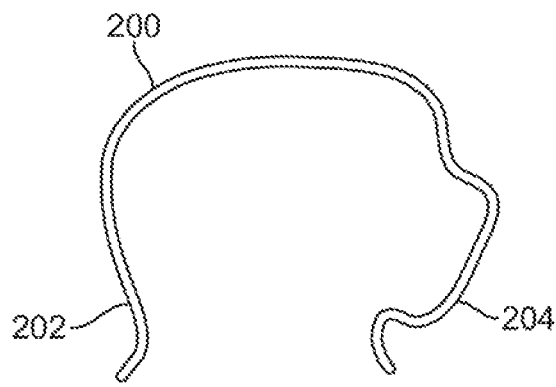
FIGS. 19A and 19B illustrate yet another variation of an oral appliance made from a shape memory material in its pre-formed relaxed configuration and its deformed configuration when placed over or upon the patient's tooth, respectively, to create an interference fit.
Figure 19B:
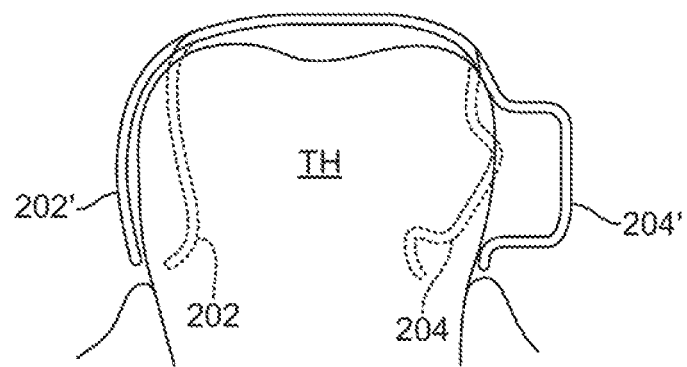

In yet another variation. FIGS. 19A and 19B illustrate an oral appliance 200 which may be pre-formed from a shape memory polymer or alloy or a superelastic material such as a Nickel-Titanium alloy, e.g., Nitinol. FIG. 19A shows oral appliance 200 in a first configuration where members 202, 204 are in an unbiased memory configuration. When placed upon or against the tooth TH, members 202, 204 may be deflected into a second configuration where members 202, 204 are deformed to engage tooth TH in a secure interference fit, as shown in FIG. 19B. The biased member 204' may be utilized to press the electronics and/or transducer assembly contained therein against the tooth surface as well as to maintain securement of the oral appliance 200 upon the tooth TH.

Figure 20:
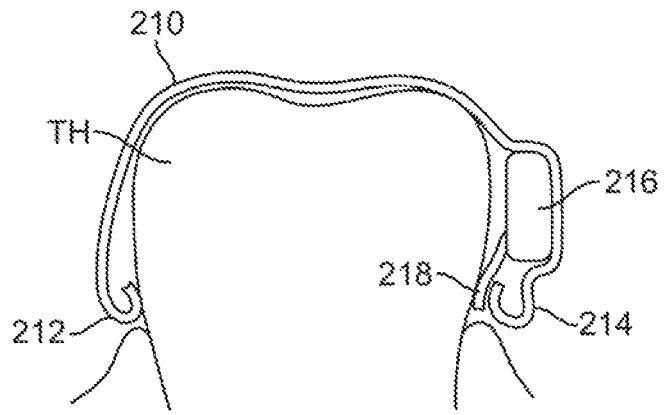
FIG. 20 illustrates yet another variation of an oral appliance made from a pre-formed material in which the transducer may be positioned between the biased side of the oral appliance and the tooth surface.

Similarly, as shown in FIG. 20, removable oral appliance 210 may have biased members to secure engage the tooth TH, as above. In this variation, the ends of the members 212, 214 may be configured into curved portions under which a transducer element 218 coupled to electronics assembly 216 may be wedged or otherwise secured to ensure mechanical contact against the tooth surface.

Figure 21:
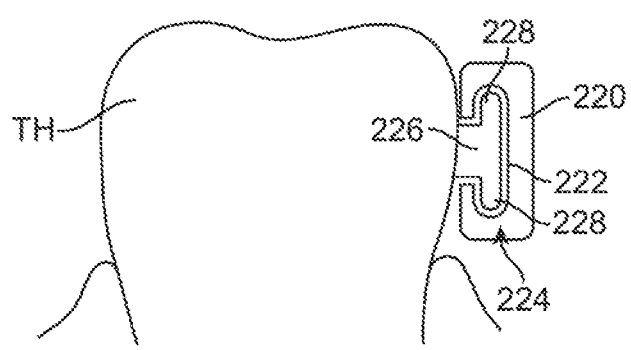
FIG. 21 illustrates a variation in which the oral appliance may be omitted and the electronics and/or transducer assembly may be attached to a composite dental anchor attached directly to the tooth surface.

FIG. 21 shows yet another variation in which the oral appliance is omitted entirely. Here, a composite dental anchor or bracket 226, as described above, may be adhered directly onto the tooth surface. Alternatively, bracket 226 may be comprised of a biocompatible material, e.g., stainless steel, Nickel-Titanium, Nickel, ceramics, composites, etc., formed into a bracket and anchored onto the tooth surface. The bracket 226 may be configured to have a shape 228 over which an electronics and/or transducer assembly 220 may be slid over or upon via a channel 222 having, a corresponding receiving configuration 224 for engagement with bracket 226. In this manner, assembly 220 may be directly engaged against bracket 226, through which a transducer may directly vibrate into the underlying tooth TH. Additionally, in the event that assembly 220 is removed from the tooth TH, assembly 220 may be simply slid or rotated off bracket 226 and a replacement assembly may be put in its place upon bracket 226.

Figure 22A:
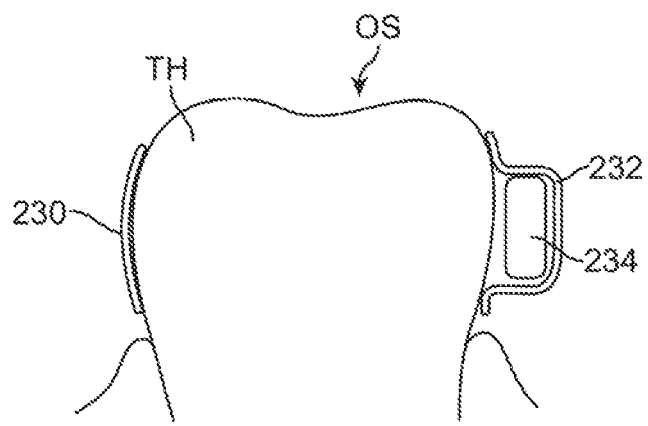
FIGS. 22A and 22B show partial cross-sectional side and perspective views, respectively, of another variation of an oral appliance assembly having its occlusal surface removed or omitted for patient comfort.
Figure 22B:
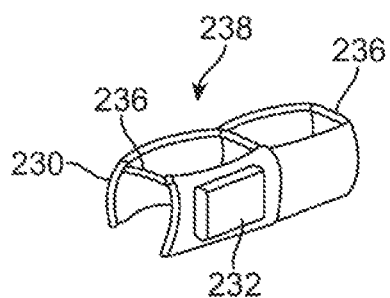

FIGS. 22A and 22B show partial cross-sectional side and perspective views, respectively, of yet another variation of an oral appliance 230. In this variation, the oral appliance 230 may be configured to omit an occlusal surface portion of the oral appliance 230 and instead engages the side surfaces of the tooth TH, such as the lingual and buccal surfaces only. The electronics and/or transducer assembly 234 may be contained, as above, within a housing 232 for contact against the tooth surface. Additionally, as shown in FIG. 22B, one or more optional cross-members 236 may connect the side portions of the oral appliance 230 to provide some structural stability when placed upon the tooth. This variation may define an occlusal surface opening 238 such that when placed upon the tooth, the user may freely bite down directly upon the natural occlusal surface of the tooth unobstructed by the oral appliance device, thereby providing for enhanced comfort to the user.

Figure 23A:
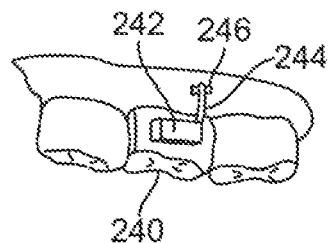
FIGS. 23A and 23B illustrate perspective and side views, respectively, of an oral appliance which may be coupled to a screw or post implanted directly into the underlying bone, such as the maxillary or mandibular bone.
Figure 23B:
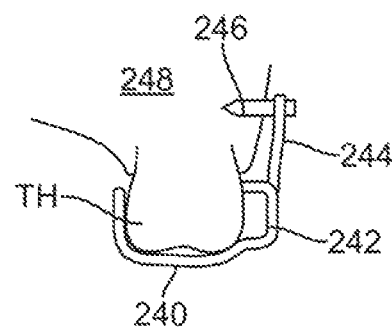

In yet other variations, vibrations may be transmitted directly into the underlying bone or tissue structures rather than transmitting directly through the tooth or teeth of the user. As shown in FIG. 23A, an oral appliance 240 is illustrated positioned upon the user's tooth, in this example upon a molar located along the upper row of teeth. The electronics and/or transducer assembly 242 is shown as being located along the buccal surface of the tooth. Rather than utilizing a transducer in contact with the tooth surface, a conduction transmission member 244, such as a rigid or solid metallic member, may be coupled to the transducer in assembly 242 and extend from oral appliance 240 to a post or screw 246 which is implanted directly into the underlying bone 248, such as the maxillary bone, as shown in the partial cross-sectional view of FIG. 23B. As the distal end of transmission member 244 is coupled directly to post or screw 246, the vibrations generated by the transducer may be transmitted through transmission member 244 and directly into post or screw 246, which in turn transmits the vibrations directly into and through the bone 248 for transmission to the user's inner ear.

Figure 24:
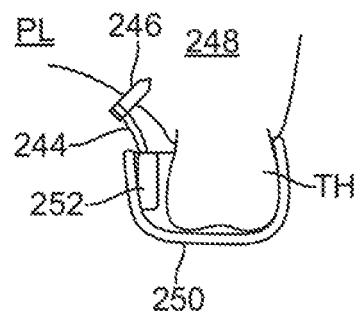
FIG. 24 illustrates another variation in which the oral appliance may be coupled to a screw or post implanted directly into the palate of a patient.

FIG. 24 illustrates a partial cross-sectional view of an oral appliance 250 placed upon the user's tooth TH with the electronics and/or transducer assembly 252 located along the lingual surface of the tooth. Similarly, the vibrations may be transmitted through the conduction transmission member 244 and directly into post or screw 246, which in this example is implanted into the palatine bone PL. Other variations may utilize this arrangement located along the lower row of teeth for transmission to a post or screw 246 drilled into the mandibular bone.

Figure 25A:
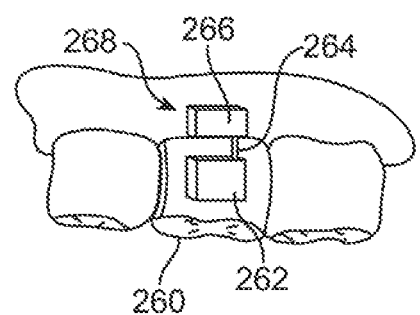
FIGS. 25A and 25B illustrate perspective and side views, respectively, of an oral appliance which may have its transducer assembly or a coupling member attached to the gingival surface to conduct vibrations through the gingival tissue and underlying bone.
Figure 25B:
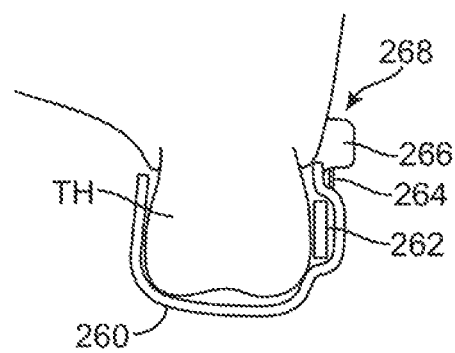

In yet another variation, rather utilizing a post or screw drilled into the underlying bone itself, a transducer may be attached, coupled, or otherwise adhered directly to the gingival tissue surface adjacent to the teeth. As shown in FIGS. 25A and 25B, an oral appliance 260 may have an electronics assembly 262 positioned along its side with an electrical wire 264 extending therefrom to a transducer assembly 266 attached to the gingival tissue surface 268 next to the tooth TH. Transducer assembly 266 may be attached to the tissue surface 268 via an adhesive, structural support arm extending from oral appliance 260, a dental screw or post, or any other structural mechanism. In use, the transducer may vibrate and transmit directly into the underlying gingival tissue, which may conduct the signals to the underlying bone.

Figure 26:
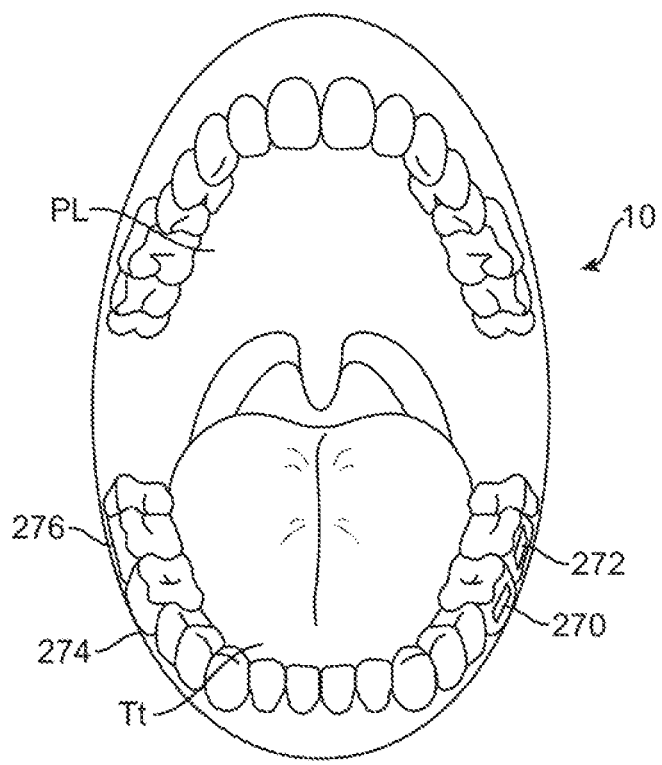
FIG. 26 illustrates an example of how multiple oral appliance hearing aid assemblies or transducers may be placed on multiple teeth throughout the patient's mouth.

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 26 illustrates one example where multiple transducer assemblies 270, 272, 274, 276 may be placed on multiple teeth. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within non-overlapping frequency ranges between each assembly. As mentioned above, each transducer 270, 272, 274, 276 can be programmed or preset for a different frequency response such that each transducer may be optimized for a different frequency response and/or transmission to deliver a relatively high-fidelity sound to the user. Moreover, each of the different transducers 270, 272, 274, 276 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user. For instance, a first transducer located, e.g., on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

Figure 27A:
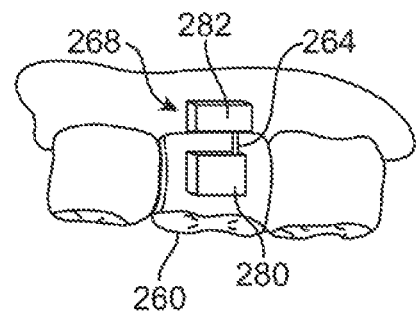
FIGS. 27A and 27B illustrate perspective and side views, respectively, of an oral appliance (similar to a variation shown above) which may have a microphone unit positioned adjacent to or upon the gingival surface to physically separate the microphone from the transducer to attenuate or eliminate feedback.
Figure 27B:
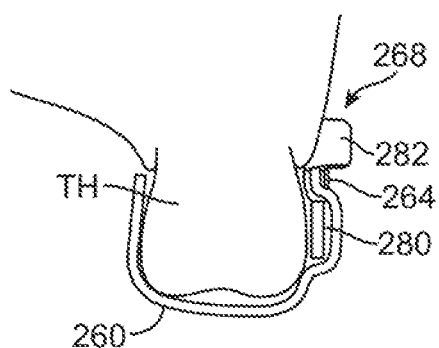

In variations where the one or more microphones are positioned in intra-buccal locations, the microphone may be integrated directly into the electronics and/or transducer assembly, as described above. However, in additional variation, the microphone unit may be positioned at a distance from the transducer assemblies to minimize feedback. In one example, similar to a variation shown above, microphone unit 282 may be separated from electronics and/or transducer assembly 280, as shown in FIGS. 27A and 27B. In such a variation, the microphone unit 282 positioned upon or adjacent to the gingival surface 268 may be electrically connected via wire(s) 264.

Figure 28:
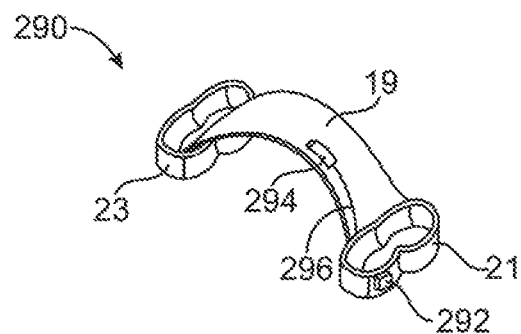
FIG. 28 illustrates another variation of a removable oral appliance supported by an arch and having a microphone unit integrated within the arch.

Although the variation illustrates the microphone unit 282 placed adjacent to the gingival tissue 268, unit 282 may be positioned upon another tooth or another location within the mouth. For instance, FIG. 28 illustrates another variation 290 which utilizes an arch 19 connecting one or more tooth retaining portions 21, 23, as described above. However, in this variation, the microphone unit 294 may be integrated within or upon the arch 19 separated from the transducer assembly 292. One or more wires 296 routed through arch 19 may electrically connect the microphone unit 294 to the assembly 292. Alternatively, rather than utilizing a wire 296, microphone unit 294 and assembly 292 may be wirelessly coupled to one another, as described above.

Figure 29:
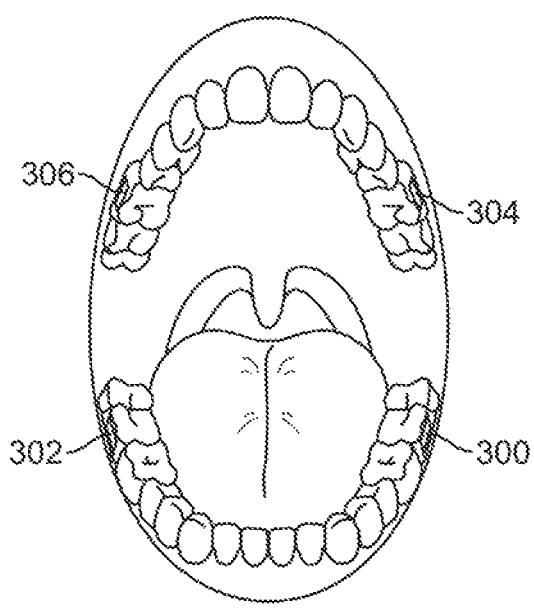
FIG. 29 shows yet another variation illustrating at least one microphone and optionally additional microphone units positioned around the user's mouth and in wireless communication with the electronics and/or transducer assembly.

In yet another variation for separating the microphone from the transducer assembly, FIG. 29 illustrates another variation where at least one microphone 302 (or optionally any number of additional microphones 304, 306) may be positioned within the mouth of the user while physically separated from the electronics and/or transducer assembly 300. In this manner, the one or optionally more microphones 302, 304, 306 may be wirelessly coupled to the electronics and/or transducer assembly 300 in a manner which attenuates or eliminates feedback, if present, from the transducer.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A bone conduction apparatus, comprising:
    a housing configured to engage at least a portion of at least one tooth of a subject;
    a transducer disposed within or upon the housing and in vibratory communication with at least one surface of the at least one tooth, wherein said apparatus produces an interference fit between the apparatus and at least two surfaces of the at least one tooth; and
    at least one microphone in communication with the transducer.

2. The apparatus of claim 1 wherein the at least one microphone is configured to be worn by the subject.

3. The apparatus of claim 1 wherein the at least one microphone has a form selected from the group consisting of a watch, necklace, lapel, phone, and belt-mounted device.

4. The apparatus of claim 1 further comprising a charger for charging the transducer.

5. The apparatus of claim 1 wherein the housing comprises an oral appliance that conforms to the at least one tooth.

6. The apparatus of claim 1 wherein the oral appliance is fabricated via a three-dimensional printing process.

7. The apparatus of claim 1 further comprising an electronic assembly disposed within or upon the housing and which is in communication with the transducer.

8. The apparatus of claim 7 wherein the electronic assembly is encapsulated within the housing.

9. The apparatus of claim 7 wherein the electronic assembly further comprises a power supply in electrical communication with the transducer.

10. The apparatus of claim 7 wherein the electronic assembly further comprises a processor in electrical communication with the transducer.

11. The apparatus of claim 7 wherein the electronic assembly further comprises a receiver in wireless communication with an externally located transmitter assembly.

12. The apparatus of claim 1 wherein the housing is comprised of a shape memory material having a pre-formed unbiased configuration and a deformed configuration whereby the housing is secured onto the at least one tooth in the deformed configuration.

13. The apparatus of claim 1 further comprising at least one additional transducer in vibratory communication with a surface of at least one additional tooth.

14. A method of transmitting vibrations via at least one tooth, comprising:
    engaging at least a portion of at least one tooth of a subject via an apparatus having a housing such that an occlusal surface of the tooth remains unobstructed by the housing and a transducer disposed within or upon the housing remains in vibratory communication with at least one surface of the at least one tooth, wherein the apparatus remains engaged via an interference fit between the apparatus and at least two surfaces of the at least one tooth;
    receiving an auditory signal via a microphone separated at a distance from the housing; and
    transmitting vibrations corresponding to the auditory signal to the surface of the at least one tooth.

15. The method of claim 14 wherein engaging at least a portion of at least one tooth comprises securing the housing against or upon the at least one tooth.

16. The method of claim 14 further comprising wirelessly linking the transducer and the microphone.

17. The method of claim 14 further comprising actuating at least one additional transducer in vibratory communication with a surface of at least one additional tooth.

* * * * *